United States Patent [19]

Kühn et al.

[11] 4,329,527
[45] May 11, 1982

[54] PROCESS FOR THE MANUFACTURE OF 1,2-DICHLOROETHANE

[75] Inventors: Wenzel Kühn; Josef Riedl, both of Burgkirchen; Peter Widmann, Altötting, all of Fed. Rep. of Germany

[73] Assignee: Hoechst Aktiengesellschaft, Fed. Rep. of Germany

[21] Appl. No.: 212,362

[22] Filed: Dec. 3, 1980

[30] Foreign Application Priority Data

Dec. 8, 1979 [DE] Fed. Rep. of Germany ....... 2949530

[51] Int. Cl.³ .............................................. C07C 17/15
[52] U.S. Cl. .................................... 570/245; 570/243
[58] Field of Search ................................. 570/245, 243

[56] References Cited

U.S. PATENT DOCUMENTS 3,267,161 8/1966 Ukaji et al. .......................... 570/245
3,288,863 11/1966 Piester .................................. 570/224
3,536,770 10/1970 Skaperdas et al. .................. 570/243
3,631,206 12/1971 Bohl et al. ........................... 570/243
3,679,373 7/1972 Van Camp et al. ................. 570/243
3,816,554 6/1974 Reni et al. ........................... 570/243
4,172,052 10/1979 Foster ................................. 570/243

Primary Examiner—Arthur P. Demers
Attorney, Agent, or Firm—Connolly and Hutz

[57] ABSTRACT

A process for the manufacture of 1,2-dichloroethane is described, in which 1 mol of ethylene, 0.35 to 0.7 mol of chlorine, 0.7 to 1.4 mol of hydrogen chloride and 0.2 to 0.6 mol of oxygen, optionally together with inert gas, are reacted in a reaction zone containing surfaces capable of being heated and cooled, at 180° to 260° C. and under a pressure of 0.09 to 1.1 MPa, in the presence of a fixed bed catalyst containing copper. The process allows better utilization of the heat generated in the chlorination of ethylene.

11 Claims, No Drawings

PROCESS FOR THE MANUFACTURE OF 1,2-DICHLOROETHANE

The invention provides a process for the manufacture of 1,2-dichloroethane as claimed in claim 1.

1,2-Dichloroethane has already been manufactured on a large industrial scale for a number of years. It is mainly converted into vinyl chloride by thermal cracking, the latter forming in turn the basis for the large-tonnage plastic polyvinyl chloride. Use for this purpose has made 1,2-dichloroethane into one of the chlorinated aliphatic hydrocarbons which are produced on the largest scale. A number of different processes are known for its manufacture, most of which start from ethylene. In general, elementary chlorine is reacted directly with ethylene in an addition reaction, this reaction being carried out at temperatures of 40° to about 120° C. in the liquid phase, frequently in 1,2-dichloroethane. In a form of this process which is much used, the considerable amount of heat formed in the addition reaction with chlorine is removed by means of boiling 1,2-dichloroethane.

In the thermal cracking of 1,2-dichloroethane to give vinyl chloride, hydrogen chloride is formed which, together with oxygen or air, is used for chlorinating further ethylene amounts. Such an oxychlorination process is generally carried out at temperatures of from 180° to 320° C. in the presence of a so-called Deacon catalyst (mostly copper chloride with additives) in the form of a fixed bed or fluidized bed.

Hitherto, direct chlorination and oxychlorination of ethylene has been carried out in separate equipment, probably because it was feared that at the relatively elevated temperatures required for an effective oxychlorination direct reaction of ethylene with chlorine would incite undesirable reactions, for example substitution reactions, instead of a simple addition reaction, and moreover the steam formed in the oxychlorination would cause further disturbances and side reactions. It was therefore preferred to carry out the direct addition of chlorine onto ethylene at considerably reduced temperatures and in liquid phase in the presence of relatively small amounts of a catalyst (mostly iron(III) chloride), and rather to put up with the disadvantageous fact that the important amount of heat is generated on an unfavorably low temperature level, so that its economic utilization is made very difficult.

In U.S. Pat. No. 3,288,868, a method for the oxychlorination of aliphatic hydrocarbons and their incompletely chlorinated derivatives in a fluidized bed of catalyst particles at temperatures of below 260° C. is described, in which the substance to be chlorinated, oxygen and elementary chlorine, hydrogen chloride, or a mixture of the latter two substances are used. Whenever ethylene is mentioned in this patent specification, hydrogen chloride and oxygen only, without elementary chlorine, are used. A mixture of chlorine and hydrogen chloride is for example recommended for the chlorination of methane, that is, a saturated hydrocarbon, where substitution reaction of the chlorine is desired.

According to German Auslegeschrift No. 1,229,999, 1,2-dichloroethane is manufactured by reacting in a first step excess ethylene, hydrogen chloride and excess oxygen in the form of air at 180° to 350° C. in the presence of a known oxychlorination catalyst, and reacting in a second step the residual gases from the first step, after unreacted hydrogen chloride has been washed off and thus a substantial part of 1,2-dichloroethane formed has condensed, with chlorine at 80° to 250° C. in the presence of an iron-containing catalyst.

Furthermore, a process for the manufacture of 1,2-dichloroethane by chlorination in the gaseous phase of ethylene-containing gases is known from German Offenlegungsschrift No. 2,649,533, according to which the reaction is carried out in the presence of copper(II) chloride and/or iron(III) chloride on a carrier as catalyst and at a temperature of from 80° to 250° C. in the catalyst layer. Preferably, gases are used for this process which contain 10% of ethylene at most, for example ethylene-containing residual gases from an oxychlorination process. Both these latter published papers relate to two-step processes which require considerable apparatus expenditure.

In German Offenlegungsschrift No. 2, 106,016, there is claimed another process for the manufacture of 1,2-dichloroethane by reaction of ethylene with oxygen and hydrogen chloride or chlorine, or a mixture of hydrogen chloride and chlorine, as chlorinating agent in a fluidized bed consisting of oxychlorinating catalyst particles, in which process the density of the fluidized bed is adjusted in such a manner that in longitudinal direction of the bed between a place about 12.7 cm above the starting point of the reaction and the upper end of the bed over its width a temperature gradient of from 11.1° to 127.8° C. is obtained. However, there are no particulars or data in the specification and the examples with respect to the oxychlorination of ethylene with oxygen and mixtures of chlorine and hydrogen chloride.

A process has now been found which allows the manufacture of 1,2-dichloroethane in one single step by chlorination and oxychlorination of ethylene, in a reaction zone containing a fixed bed catalyst, wherein in view of the later thermal decomposition of 1,2-dichloroethane to give vinyl chloride the chlorination agents can be used in a favorable molar ratio.

Subject of the invention is a process for the manufacture of 1,2-dichloroethane by reaction of ethylene with chlorine, hydrogen chloride and oxygen or oxygen-containing inert gases, at 180° to 260° C. and a pressure of from 0.09 to 1.1 MPa, in the presence of a copper (chloride)—containing fixed bed catalyst, in a reaction zone containing surfaces capable of being heated and cooled; the gaseous reaction mixture being removed from the reaction zone after passage through the fixed bed catalyst, cooled, and the 1,2-dichloroethane formed being separated according to known methods; which comprises introducing into the reaction zone ethylene, chlorine and oxygen or oxygen-containing inert gases before the fixed catalyst bed, and hydrogen chloride either at the same place as said other gases or in the first third of the fixed catalyst bed at the latest, in the following quantitative ratio: 1 mol $C_2H_4$:0.35 to 0.7 mol $Cl_2$:0.7 to 1.4 mol HCl:0.2 to 0.6 mol $O_2$.

By inert gases, there are to be understood substances which are gaseous under the reaction conditions and either do not take part in the reaction at all or to an insignificant extent only. Examples are nitrogen, carbon dioxide, and noble gases. Preferably, nitrogen in admixture with oxygen is used, especially air and mixtures of air and oxygen.

The reaction is carried out at a temperature of from 180° to 260° C. Generally, the maximum temperature in the reaction zone is measured in the first fourth of the catalyst bed (in the direction of gas flow). In principle, this temperature may prevail all over the catalyst bed; but often a drop in temperature is observed in the direction of gas flow, so that at the end of the catalyst bed a temperature is measured which is lower by 5° to 50° C. than that prevailing at the place of the maximum.

Below 180° C., poor yields are obtained, and above 260° C., impurities and by-products increase considerably, which likewise reduces the yield and, moreover, requires increased expenditure for obtaining a pure 1,2-dichloroethane. Preferably, the operations are carried out in a temperature range of from 190° to 240° C., especially 200° to 230° C.

The pressure in the reaction zone is advantageously from 0.09 to 1.1 MPa. Below normal atmospheric pressure, that is, below 0.09 MPa, apparatus cost increases and space/time yields decrease. Above 1.1 MPa, the space/time yield continues to increase, but this advantage is annihilated by additional apparatus expenditure. Preferably, operations are carried out in a pressure range of from 0.3 to 0.6 MPa.

Advantageously, the reaction zone is substantially filled with the fixed bed catalyst, that is, at a rate of 75% and more. In the reaction zone, advantageously above all in the fixed bed catalyst which generally consists of a packing of catalyst particles, there are arranged surfaces capable of being heated and cooled. Generally, the reaction vessel containing the reaction zone is provided with a double jacket. This is sufficient in the case where the reaction zone is very slender, that is, when the ratio of its cross-sectional area to its length is 0.008 m$^2$/m or less. When the ratio of cross-sectional area to length is substantially superior, it is advisable to use inserts; vertically positioned plates or tubes, for example, being suitable. The double jacket, the tubes or plates contain a tempering medium flowing in their interior. When for example vertical tubes are used as inserts, the tempering medium may be in the tubes and the catalyst outside thereof, or inversely, the catalyst may be in the tubes and the tempering medium outside thereof. In this latter case, the double jacket may be omitted.

As tempering medium, liquids and/or gases are used, advantageously in such a manner that the dissipated heat of reaction can be economically utilized. Examples of tempering liquids are high temperature-resistant oils, especially silicone oils, or optionally water or 1,2-dichloroethane which vaporize. Suitable gaseous substances are air or ethylene which after having been heated are used in the reaction process, or steam or 1,2-dichloroethane vapor.

Ethylene, chlorine and oxygen or oxygen-containing inert gas are introduced into the reaction zone at a place before the catalyst bed. Advantageously, ethylene and chlorine are fed in separately from each other, while oxygen or oxygen-containing inert gases can be fed in together with the chlorine. In any case, care has to be taken that in the reaction zone the gases are thoroughly intermixed. This can be ensured for example by providing the corresponding end of the inlet tube with a device for distribution of the gases all over the area of the reaction zone, for example a frit or perforated plate. Furthermore, it may be advantageous to place a packing of inert particles below the catalyst bed, which particles may have the same size and shape as the catalyst-containing ones, and which likewise ensure a homogeneous distribution of the gases.

In addition to the above gases, hydrogen chloride is fed in, at the latest in the first third of the catalyst bed in the direction of gas flow. Alternatively, it may be fed in before, for example into the above packing of inert particles, or advantageously together with the ethylene, while passing through a distributor device.

The gases as indicated in the previous paragraphs are introduced in the following quantitative ratio: 1 mol $C_2H_4$:0.35 to 0.7 mol $Cl_2$:0.7 to 1.4 mol HCl:0.2 to 0.6 mol $O_2$, which is especially favorable in view of the further application of the 1,2-dichloroethane obtained for the manufacture of vinyl chloride by thermal cracking, and reuse of the hydrogen chloride formed in this process. This molar ratio endures good yields of 1,2-dichloroethane without substantial formation of by-products, especially when no more than about 2 chlorine atoms (calculated on the sum of chlorine and hydrogen chloride) are used per mol of ethylene. Preferably, operations are carried out at the following ratio: 1 mol $C_2H_4$:0.40 to 0.55 mol $Cl_2$:0.9 to 1.2 mol HCl:0.25 to 0.4 mol $O_2$. As already mentioned, the oxygen can be introduced into the process in the form of air or mixtures of air and oxygen.

Moreover, it is advantageous to use a small excess, that is, about 125 to 180% by volume, of the stoichiometric amount of oxygen necessary for the reaction. Thus, the yield relative to the other gases is improved, and difficulties in the work-up of the reaction mixture which could cause increased apparatus expenditure are avoided, especially in the case where air is used as oxygen source.

It is furthermore advantageous to employ an excess of ethylene relative to the chlorine-containing gases, which is chosen in such a manner that from 1.8 to 1.99 chlorine atoms are present per 1 mol of ethylene, calculated on the sum of $Cl_2$ and HCl. Thus, troubles due to corrosion and side reactions are avoided.

The fixed bed catalyst consists preferably of a packing of particles having a size of from 0.1 to 15, preferably 1 to 7 mm. The individual particles may have various shapes; they may be for example spherical, square, cubic or cylindrical, and have the form of rods, hemispheres or rings.

The catalyst may consist of particles of the same composition; preferably, however, it contains particles of different composition. It is not required that all particles contain copper, on the contrary, especially in the case of fixed beds in large vessels having a relatively high ratio of volume to surface it is advisable to add to the copper-containing catalyst particles inert particles consisting of a substance which at 200° C. has a coefficient of thermal conductivity of at least 400 $Jh^{-1}cm^{-1}K-1$. Suitable substances are for example graphite or metals or metal alloys which react with the gaseous mixture either not at all or to an insignificant extent only under the reaction conditions, such as nickel, silver, nickel alloys or nickel steels having a relatively high nickel content. Interesting results are obtained when from 25 to 75% by volume, relative to the volume of all particles of the fixed bed, consist of these inert particles. Below 25% by volume, the heat conductivity is generally not increased, and above 75% by volume, the activity of the catalyst is considerably reduced, probably because of a too high dilution rate.

The particles of the fixed catalyst bed which contain the catalyst as such consist preferably of porous aluminum oxide or silicon dioxide, or mixtures of these two oxides, onto which the copper, generally in the form of a copper compound, mostly copper chloride, is applied by precipitation. The catalyst particles may alternatively contain other copper salts, for example nitrate or acetate, or other copper compounds; however, they are generally converted to copper chloride when the catalyst is in operation.

It is advantageous to use a catalyst bed which, in the direction of gas flow, has a continuously or gradually rising copper concentration, thus ensuring better distribution of heat over the whole catalyst and better dissipation of reaction heast as a consequence. The increase of copper concentration in the direction of gas flow should be adjusted in such a manner that the catalyst bed, on entry of the gases, contains at least 1, preferably from 3 to 8, weight % of copper, and at most 20, preferably 4 to 12, weight % of copper when the gases are leaving. Below 1 weight % of copper, the catalytic action is too poor, above 20 weight % of copper the catalyst is ofter insufficiently porous for the contact of an intended large surface with the reaction mixture; moreover, there is an increased risk of volatile copper compounds being eliminated from the reaction zone together with the reaction mixture. In case of additional use of particles of inert material having a good thermal conductivity as described above, the copper concentration of the catalyst-containing particles must be correspondingly increased in order to attain the aforementioned values relative to the whole fixed bed. However, even in this case the copper concentration of the catalyst-containing particles should not exceed 20 weight %.

In addition to copper, the catalyst particles contain advantageously at least one of the following compounds: sodium chloride, potassium chloride, calcium chloride or magnesium chloride, which addition improves the activity of the catalyst and reduces the volatility of the copper compounds. The amount to be added depends on the copper content, and is generally from about 25 to 120 weight %, relative to the copper portion of the catalyst.

The activity of the catalyst particles can be further increased by adding from 0.001 to 1% by weight, relative to the total weight of the fixed bed, of iron, which may be present in the form of a compound capable of being converted to iron chloride under the reaction conditions. Alternatively to iron chloride, another Lewis acid may be employed.

The catalyst may contain in addition further materials which improve the activity and/or selectivity of the catalyst in respect of the production of 1,2-dichloroethane. Examples which may be mentioned are silver, zinc, chromium, manganese, rare earth metals, such as cerium, lanthanum, ytterbium and neodymium, and platinum metals, such as rhodium and platinum.

Advantageously, the fixed catalyst bed has a free gas space of from 15 to 60, preferably 20 to 45% by volume. Below 15% by volume, the pressure in the catalyst bed decreases to such an extent that the gas throughput required for economic operation cannot be ensured. On the other hand, a catalyst bed having more than 60% by volume of free gas space necessitates a complicated shape of the individual catalyst particles, reduces considerably the mechanical stability of the catalyst, requires a larger reaction vessel and thus increased investment cost, and furthermore hinders the dissipation of heat within the catalyst. The free gas space of a fixed bed catalyst can be determined for example as follows: precisely 2 liters of catalyst particles are charged to a cylindrical graduated recipient, and the recipient and its charge are weighed. Subsequently, water is added until the water level has reached the surface of the packing of catalyst particles. The cylindrical recipient is slightly shaken from time to time during this operation in order to allow enclosed air to escape. Thereafter, the recipient and its content are weighed again, and the difference of weight in grams corresponds practically to the cubic centimeters of free gas space in the packing of catalyst particles.

From 75 to 98, preferably 85 to 95% by volume of the reaction zone are filled with the fixed catalyst bed.

The average residence time of the gases fed to the reaction zone is generally from 4 to 50, preferably 7 to 25, seconds. Below 4 seconds, the conversion rate is poor, above 50 seconds the process cannot be carried out but with a considerably reduced space/time yield, so that it becomes uneconomic.

After having left the catalyst bed, the reaction mixture is cooled as usual, and the 1,2-dichloroethane is liberated from unreacted reactants, inert gases and by-products by partial condensation or distillation.

As already mentioned above, the process of the invention allows to react ethylene, in one single reaction zone and in the presence of a fixed bed catalyst, with chlorine, hydrogen chloride and oxygen in quantitative amounts which are especially favorable in view of the later thermal cracking of 1,2-dichloroethane for the manufacture of vinyl chloride. 1,2-Dichloroethane is obtained with high yields without substantial amounts of disturbing by-products. There is furthermore a good conversion rate with respect to chlorine and hydrogen chloride; the chlorine present in the reaction mixture is converted completely to 1,2-dichloroethane. The new process does not require much apparatus expenditure, and the reaction heat produced by the chlorination of ethylene is on a temperature level which allows interesting reuse of energy, for example for heating distillation equipment.

The following examples illustrate the invention.

EXAMPLE 1

The following apparatus is used: a vertical glass tube with an internal diameter of 50 mm, narrowed at the bottom and at the top to form a gas inflow aperture and a gas outflow aperture, respectively, is used for carrying out the conversion of ethylene into 1,2-dichloroethane. This vertical reaction tube contains, immediately above the lower inflow aperture, a glass frit which extends over the whole internal cross-section of the reaction tube. A second frit is mounted a short distance above this first frit; its area amounts to about half the cross-section of the reaction tube and it is connected in its lower section to a glass tube which is passed laterally through the wall of the reaction tube. For temperature control, the reaction tube contains a coiled glass tube, the connections of which are also passed laterally through the wall of the reaction tube and which begins above the second frit and reaches a height in the reaction tube such that about 5/100 of the total length of the reaction tube, in the upper section, remain free. Two partitions in the form of perforated plates are mounted in the reaction tube in identical distance from each other and from the top and the bottom of the tube. Furthermore, the jacket of the reaction tube contains 4 sockets, three of which are positioned approximately in the center of the compartments shaped by the two partitions. The 4th socket is positioned nearly immediately below the first partition, somewhat below the first third of the reaction tube (in the direction of gas flow). The reaction tube is further provided with 4 temperature control devices which are also passed through the jacket. Two of these thermocouples are arranged below the first partition (in the direction of gas flow): the first thermocouple is positioned in the first fourth of the total reaction tube (in the direction of gas flow), and the second one nearly immediately below the first partition. The two other thermocouples are placed each in the center of the second and last, respectively, third of the reaction tube (in the direction of gas flow).

In its lower third, the reaction tube is provided with a double jacket through which gases or liquids can be passed; in the central and upper third, the jacket is heat-insulated. The length of the reaction zone, measured from the surface of the first frit to the taper in the upper part of the reaction tube is 750 mm.

The gas discharge tube from the upper part of the reaction tube is connected via a descending duct to a water condenser, at the lower end of which is attached a condensate receiver with a drain cock. In its upper section, the condensate receiver contains a gas discharge tube which in turn leads into an ascending brine condenser. The constituents of the gas which are condensed here flow into a second condensate receiver with a drain cock. The non-condensable exit gases leaving the upper section of the brine condenser are passed through wash bottles in in order to trap the hydrogen chloride contained therein. Samples of the washed exit gas are withdrawn for analysis by gas chromatography. The condensates which collect in the two vessels mounted below the condensers are combined and are also analyzed by gas chromatography. The connecting tube from the reaction tube to the first condenser is provided with a heating sleeve and heated sufficiently to prevent condensate being formed therein.

The volume of the reaction zone in the reaction tube, deducting the fitments contained therein (the heat control coil, the second frit, and the thermocouples) is 1150 cm$^3$.

For carrying out Example 1, a catalyst is charged to the reaction tube which contains copper chloride in varying concentration on aluminum oxide, and which consists of cylindrical particles the bottom and top surfaces of which have a diameter of 4.3 mm each, and the convex surface line of which has a length of 4.3 mm. The lower third of the reaction tube up to the first partition is filled with catalyst particles containing 3.7 weight % of copper, about 3.3 weight % of potassium chloride and about 0.005 weight % of iron (all weight percentages being relative to the total weight of the catalyst particles). The central third of the reaction tube between the two partitions is filled with a catalyst containing 5.1 weight % of copper, about 3.3 weight % of potassium chloride and about 0.005 weight % of iron. The upper third is filled with catalyst particles containing 7.8 weight % of copper, 3.3 weight % of potassium chloride and about 0.005 weight % of iron. For each third of the reaction tube 0.35 l of catalyst particles are used, so that the total packing of the tube is 1.05 l, that is, 91.3% by volume of the total reaction zone at disposal. The free gas volume of the catalyst particle packing is adjusted to 35% by volume according to the water displacement method.

First, hot oil is passed through the coiled glass tube, so that the catalyst is heated to about 190° C. An amount of 40 standard liters per hour of air and of 10 standard liters per hour of chlorine is fed to the reaction tube through the first frit via the lower gas inlet tube. Simultaneously, the reaction tube is charged through the second frit with a mixture of 22 standard liters of ethylene per hour and 24 standard liters per hour of gaseous hydrogen chloride. The molar ratio of the gases fed in is 1 mol C$_2$H$_4$:0.435 mol Cl$_2$:1.044 mol HCl:0.365 mol O$_2$ (in the form of air). Relative to the stoichiometric amount necessary for oxydation of the hydrogen chloride (=100% by volume), the oxygen excess is 139.4% by volume. The amount of chlorine and hydrogen chloride is chosen in such a manner that 1.9 chlorine atoms are present per molecule of ethylene.

Together with the introduction of the reaction gases, the water condenser is fed with water at +14° C. and the brine condenser is fed with cooling brine at −15° C. The exit gas wash bottles contain water as the washing liquid. After a short time, a temperature rise to about 230° C. is stated at the thermocouple in the first fourth of the reaction tube. Already during this time, the temperature of the oil flowing through the coiled glass tube is constantly decreased and after about ½ hour adjusted in such a manner that the following temperatures are measured at the four temperature control devices $T_1$ to $T_4$ (in the direction of gas flow): $T_1$=243° C., $T_2$=217° C., $T_3$=215° C., $T_4$=212° C., which are kept constant within the following 3 hours. If necessary in order to maintain these temperatures, cooling air is additionally blown through the double jacket in the lower third of the reaction tube. The exit gas leaving the brine condenser has a temperature of 12° C.

The experiment is continued for 3 hours and the exit gas composition of the washed exit gas is determined by gas chromatography after ⅓ of this period and again after ⅔ of this period. A thermal conductivity detector is used for the gases oxygen, carbon monoxide, carbon dioxide and ethylene, while a flame ionization detector is used for all the other gases indicated below. The mean values from the two analyses are listed for all the examples in Table II which follows later in the text, the proportion of rare gas brought in via the air used having been already deducted from the oxygen figure.

At the end of the running time of the experiment, the gas supply to the reaction tube is terminated and the catalyst is cooled by blowing with air of room temperature. The condensate formed in the water condenser and the brine condenser is combined, weighed and similarly analyzed by gas chromatography by means of a flame ionization detector. The values determined for the individual Examples are listed in Table I which follows later in the text.

The following values are calculated for the experiment according to Example 1:

Conversion: 86%, relative to HCl; 100%, relative to Cl$_2$; 91%, relative to C$_2$H$_4$. Space-time-yield (relative to a reaction space of 0.45 l): 221.25 g of crude 1,2- dichloroethane·h$^{-1}$.l$^{-1}$. Average residence time of the gases in the reaction zone: 8.0 seconds.

EXAMPLE 2

The same apparatus is used as in Example 1 and the procedure followed is exactly the same as indicated in that example, with the difference that the temperature in the lower fourth of the catalyst bed in the reaction tube is kept at 220° C. for a running time of the experiment totalling 3.5 hours.

The following values are determined: Molar ratio: 1 mol C$_2$H$_4$:0.435 mol Cl$_2$:1.044 mol HCl:0.365 mol O$_2$ (in the form of air). O$_2$ excess and ratio of ethylene to chlorine as in Example 1.

Temperatures: $T_1=220°$ C., $T_2=217°$ C., $T_3=214°$ C., $T_4=198°$ C. Conversion, relative to: HCl =98%, $Cl_2=100\%$, $C_2H_4=98.5\%$. Space/time yield (relative to 0.45 l of reaction space) =239.5 g of crude 1,2- dichloroethane $\cdot h^{-1} \cdot -1^{1}$. Average residence time of the gases in the reaction zone: 7.9 seconds. Analyses see Tables I and II.

EXAMPLE 3

Operations are again as in Examples 1 and 2, with the difference however that the hydrogen chloride is not introduced into the reaction zone via the second frit, but via a tube having a ball-shaped perforated terminal cover and which is passed into the reaction tube through the socket mounted laterally to the jacket in position below the first partition.

The temperature measured in the first fourth of the catalyst bed is maintained at 235° C. Test duration: 3 hours ¾. The following values are determined: Temperatures: $T_1=235°$ C., $T_2=228°$ C. $T_3=219°$ C., $T_4=217°$ C. Conversion, relative to: HCl=85%, $Cl_2=100\%$, $C_2H_4=91\%$. Space/time yield (relative to 0.45 l of reaction space): 221.5 g of crude 1,2-dichloroethane $\cdot h^{-1} \cdot l^{-1}$. Average residence time of the gases in the reaction zone: 7.8 seconds. Analyses see Tables I and II.

EXAMPLE 4

The same apparatus is used as in Example 1; however, identical catalyst particles are charged to all three compartments of the reaction tube, that is, cylindrical particles the top and bottom surfaces of which have a diameter of 4.3 mm each, and the convex surface line has a length of 4.3 mm. They consist of aluminum oxide containing 7.8 weight % of copper (as copper chloride), 3.3 weight % of potassium chloride and 0.005 weight % of iron; all weight percentages being relative to the total weight of the catalyst particles. A total of 1.05 l of catalyst particles is charged. The catalyst packing takes 91.3% by volume of the reaction tube. All other operations are as described in Example 1; the temperature in the first fourth of the fixed catalyst bed being adjusted to 241° C. Test duration: 2.5 hours. The following values are determined: Temperature: $T_1=241°$ C., $T_2=216°$ C., $T_3=212°$ C., $T_4=199°$ C. Conversion, relative to: HCl=89%, $Cl_2=100\%$, $C_2H_4=94\%$. Space/time yield (relative to 0.45 l of reaction space): 228.75 g of crude 1,2-dichloroethane $\cdot h^{-1} \cdot l^{-1}$. Average residence time of the gases in the reaction zone: 8.1 seconds. Analyses see Tables I and II. Examples 1 to 4 are carried out under normal atmospheric pressure.

EXAMPLE 5

The apparatus used for this example is set up analogously to that used in Example 1, but with the difference that the reaction vessel used is a vertical nickel tube with an internal diameter of 50 mm which is equipped similarly to the glass tube of the apparatus used in Example 1, but with the following differences: there are only three temperature measuring points the first of which is fitted in the first fourth of the catalyst bed (in the direction of gas flow), the second in the center and the third in the last fourth of the catalyst bed. The perforated partitions are omitted. A pressure-reducing valve with pressure regulator is arranged in the gas outlet tube at the head of the reactor. There is a free reaction space of 1.5 l in the tube, into which identical portions of 0.45 l each of cylindrical catalyst particles are introduced one after the other, which particles have a top and bottom surface of a diameter of 4.3 mm each and a convex surface line with a length of 4.3 mm. The kind of catalyst particles is as described in Example 1, that is, the first portion contains 3.7, the second 5.1 and the third 7.8 weight % of copper, relative to the total weight of the catalyst particles. The free space at disposal for gas reaction is 0.62 l.

A water condenser and a brine condenser and also a hydrogen chloride washer are attached, as described in Example 1, at the reactor outlet after the pressurereducing valve. Before starting the test, the fixed catalyst bed in the reaction tube is heated to 190° C. by means of the coiled nickel tube. Subsequently, 120 standard liters/hour of air and 30 standard liters/hour of gaseous chlorine are fed in under pressure via the lower gas inlet duct and frit 1; a pressure of 0.4 MPa is adjusted in the reactor by regulating accordingly the pressure-reducing valve at the head of the reactor, and maintained during the total test time. Simultaneously, 63 standard liters/hour of ethylene and 60 standard liters/hour of gaseous hydrogen chloride are introduced under pressure into the reaction tube via frit 2. The molar ratio of the gases introduced is 1 mol $C_2H_4$:0.476 mol $Cl_2$:0.956 mol HCl:0.4 mol $O_2$ (as air). The $O_2$ excess exceeding the stoichiometric amount necessary for oxydizing the hydrogen chloride is 168% by volume. 1.9 chlorine atoms per molecule of ethylene are fed in.

During the whole duration of the experiment, that is, 5 hours, water at $+14°$ C. flows through the water condenser and cooling brine at $-18°$ C. flows through the brine condenser. The exit gas leaving the brine condenser has a temperature of $+12°$ C.

About 25 minutes after the start of the test, a temperature of 235° C. had adjusted in the first fourth of the catalyst bed, which is maintained in the further course of the test by cooling of the coiled nickel tube, as described in Example 1. The following temperatures are measured: $T_1=235°$ C., $T_2=225°$ C., $T_3=218°$ C.

After ⅓ and ⅔ of the total duration of the experiment, samples of exit gas after the hydrogen chloride washing are subjected to analysis by gas chromatography. The mean value of the results obtained is listed in Table II which follows.

After the end of the experiment, the liquids condensed from the water condenser and the brine condenser are combined, weighed and then analyzed by gas chromatography. The analytical result is listed in Table I which follows. The following values are determined:

Conversion, relative to: HCl=98%, $Cl_2=100\%$, $C_2H_4=99\%$.

Space/time yield (relative to 0.62 l of reaction space): 498 g of crude 1,2-dichloroethane $\cdot h^{-1} \cdot l^{-1}$.

Average residence time of the gases in the reaction zone: 9.8 seconds. Analyses see Table I and II.

EXAMPLE 6

The apparatus is used as described in Example 1, and operations are also as indicated there, with the following differences: The temperature in the lower fourth of the fixed catalyst bed in the reaction tube is maintained at about 220° C. for a test time of 2.75 hours. The catalyst particles contain 11 weight % of copper, about 5.7 weight % of potassium chloride and 0.5 weight % of iron. The lower third of the reaction tube is filled with a mixture of 60 weight % of the catalyst particles as described and 40 weight % of glass balls having a diameter of 4.5 mm, the central part of the reaction tube contains 70 weight % of catalyst particles and 30 weight % of the cited glass balls, and the upper third 80 weight % of catalyst particles and 20 weight % of glass balls.

After heating of the catalyst, 40 standard liters/ hour of air and 10 standard liters of chlorine per hour are fed to the reaction tube via the lower gas inlet duct and the first frit. Simultaneously, a mixture of 23 standard liters/hour of ethylene and 24 standard liters/hour of gaseous hydrogen chloride are charged to the reaction tube through the second frit. The molar ratio of the gases fed in is the following: 1 mol $C_2H_4$:0.45 mol $Cl_2$:1.1 mol HCl:0.38 mol $O_2$ (in the form of air). Relative to the stoichiometric amount necessary for oxydation of the hydrogen chloride (=100% by volume), the excess of oxygen is 138% by volume. The amount of chlorine and hydrogen chloride is chosen in such a manner that 2 chlorine atoms are present per molecule of ethylene.

The following values are determined:

Temperatures: $T_1=219°$ C., $T_2=220°$ C., $T_3=224°$ C., $T_4=202°$ C.

Conversion, relative to: HCl=98%, $Cl_2=100\%$, $C_2H_4=99\%$.

Space/time yield (relative to 0.45 l of reaction space): 240.7 g of crude 1,2-dichloroethane $\cdot h^{-1} \cdot l^{-1}$.

catalyst, 40 standard liters/hour of air and 14 standard liters/hour of chlorine are fed to the reaction tube via the lower gas inlet duct and through the first frit; simultaneously, a mixture of 27 standard liters/hour of ethylene and 24 standard liters/hour of hydrogen chloride is introduced into the reaction tube through the second frit. The molar ratio of the gases fed in is the following: 1 mol $C_2H_4$:0.54 mol $Cl_2$:0.92 mol HCl:0.32 mol $O_2$ (in the form of air). Relative to the stoichiometric amount necessary for oxydation of the hydrogen chloride, the oxygen excess is 139% by volume. The amount of chlorine and hydrogen chloride is chosen in such a manner that 2 chlorine atoms are present per molecule of ethylene. During a reaction time of 3.15 hours, the following values are determined:

Temperatures: $T_1=218°$ C., $T_2=222°$ C., $T_3=223°$ C., $T_4=200°$ C.

Conversion, relative to: HCl=95%, $Cl_2=100\%$, $C_2H_4=91\%$.

Space/time yield (relative to 0.45 l of reaction space): 282 g of crude 1,2-dichloroethylene $\cdot h^{-1} \cdot l^{-1}$.

Average residence time of the gases in the reaction zone: 7.5 seconds.

Analyses see Tables I and II.

TABLE I

Gaschromatography analysis of the condensed crude 1,2-dichloroethane

| Components | Example No. 1 weight % | Example No. 2 weight % | Example No. 3 weight % | Example No. 4 weight % | Example No. 5 weight % | Example No. 6 weight % | Example No. 7 weight % |
|---|---|---|---|---|---|---|---|
| 1,2-dichloroethane | 98.91 | 99.26 | 98.78 | 99.03 | 98.06 | 99.22 | 99.12 |
| Total of: $C_2H_2$, $C_2H_4$, $C_2H_6$; | 0.0284 | 0.0273 | 0.0184 | 0.028 | 0.0053 | 0.0128 | 0.0413 |
| vinylchloride | 0.0046 | 0.0049 | 0.0041 | 0.0055 | 0.0014 | 0.0024 | 0.0057 |
| $C_2H_5Cl$ | 0.0429 | 0.0282 | 0.0295 | 0.0406 | 0.0093 | 0.0475 | 0.0319 |
| 1,1-dichloroethylene | 0.0074 | 0.0012 | 0.0019 |  | 0.0004 |  | 0.0005 |
| trans-1,2-dichloroethylene | 0.0014 | 0.0042 | 0.0022 | 0.004 | 0.0087 | 0.001 | 0.0008 |
| 1,1-dichloroethane | 0.0047 | 0.0039 | 0.0054 | 0.0031 | 0.0053 | 0.0033 | 0.004 |
| $CCl_4$ | 0.1041 | 0.0730 | 0.0897 | 0.163 | 0.0836 | 0.1266 | 0.1938 |
| cis-1,2-dichloroethylene | 0.0084 | 0.0108 | 0.0046 | 0.0233 | 0.0446 | 0.007 | 0.0059 |
| $CHCl_3$ | 0.0543 | 0.0453 | 0.0420 | 0.0857 | 0.0728 | 0.0238 | 0.0435 |
| 1,1,2-trichloroethylene | 0.0039 | 0.0053 | 0.0017 | 0.0076 | 0.0101 | 0.0024 | 0.0025 |
| 1,1,2-trichloroethane | 0.2820 | 0.2485 | 0.5894 | 0.433 | 1.0795 | 0.1948 | 0.1481 |
| 2-chloroethanol | 0.0164 | 0.0155 | 0.0211 | 0.0081 | 0.0063 | 0.008 | 0.0076 |
| 1,1,2,2-tetrachloroethane | 0.0047 | 0.0095 | 0.0350 | 0.0131 | 0.3011 | 0.0046 | 0.004 |
| chloral | 0.5200 | 0.2530 | 0.3678 | 0.156 | 0.297 | 0.345 | 0.394 |

TABLE II

Gaschromatography analysis of the exit gas after the hydrogen chloride washing

| Components | Example No. 1 vol. % | Example No. 2 vol. % | Example No. 3 vol. % | Example No. 4 vol. % | Example No. 5 vol. % | Example No. 6 vol. % | Example No. 7 vol. % |
|---|---|---|---|---|---|---|---|
| $O_2$ | 0.2 | 1.0 | 2.8 | 0.15 | 4.9 | 3.4 | 1.0 |
| CO | 3.1 | 2.1 | 2.5 | 3.3 | 1.4 | 1.4 | 2.3 |
| $CO_2$ | 3.5 | 2.3 | 2.8 | 3.0 | 2.7 | 1.7 | 2.8 |
| $C_2H_4$ | 4.9 | 1.5 | 5.7 | 3.0 | 1.2 | 1.4 | 3.8 |
| vinylchloride | 0.022 | 0.021 | 0.0185 | 0.0275 | 0.0215 | 0.0125 | 0.028 |
| $C_2H_5Cl$ | 0.074 | 0.041 | 0.043 | 0.09 | 0.072 | 0.075 | 0.059 |
| low-boiling substances | 0.005 | 0.004 | 0.004 | 0.012 | 0.0165 | 0.005 | 0.004 |
| 1,2-dichloroethane(EDC) | 3.3 | 3.3 | 3.15 | 4.1 | 4.5 | 3.8 | 3.1 |
| High-boiling substances | — | — | — | — | — | — | — |
| 1,1,2-trichloroethane | 0.002 | 0.0015 | 0.004 | 0.006 | 0.006 | 0.0015 | 0.002 |
| $Cl_2$ in the exit gas | none | none | none | none | none | none | none |
| $Cl_2$ in the water | " | " | " | " | " | " | " |
| $Cl_2$ in the crude EDC | " | " | " | " | " | " | " |

Average residence time of the gases in the reaction zone 7.9 seconds. Analysis see Tables I and II.

EXAMPLE 7

Operations are as described in Example 6 with the use of the same fixed catalyst bed. After heating of the

What is claimed is:

1. A process for the manufacture of 1,2-dichloroethane by reaction of ethylene with chlorine, hydrogen chloride and oxygen or oxygen-containing inert gases, at 180° to 260° C. and a pressure of from 0.09 to 1.1 MPa, in the presence of a copper-containing fixed bed catalyst, in a reaction zone containing surfaces capable of being heated and cooled; the gaseous reaction mixture being removed from the reaction zone after passage through the fixed bed catalyst, cooled, and the 1,2-dichloroethane formed being separated according to known methods; which comprises introducing into the reaction zone ethylene, chlorine and oxygen or oxygen-containing inert gases before the fixed catalyst bed, and hydrogen chloride either at the same place as said other gases or in the first third of the fixed catalyst bed at the latest, in the following quantitative ratio: 1 mol $C_2H_4$ :0.35 to 0.7 mol $Cl_2$:0.7 to 1.4 mol HCl:0.2 to 0.6 mol $O_2$.

2. The process as claimed in claim 1, which comprises operating at temperatures of from 190° to 240° C.

3. The process as claimed in claim 1 or 2, wherein in the fixed catalyst bed the concentration of copper is increased continuously or in steps in the direction of gas flow from at least 1 weight % to 20 weight % at most, each relative to the total weight of the fixed bed.

4. The process as claimed in one of claim 1 or 2, wherein the copper is applied by precipitation onto porous aluminum oxide or silicon dioxide or mixtures of these two oxides.

5. The process as claimed in one of claim 1 or 2, wherein the fixed bed catalyst contains in addition to copper at least one of the following compounds: sodium chloride, potassium chloride, calcium chloride or magnesium chloride.

6. The process as claimed in one of claim 1 or 2, wherein the fixed bed catalyst contains iron in amounts of from 0.001 to 1 weight %, relative to the total weight of the fixed bed.

7. The process as claimed in one of claim 1 or 2, wherein the fixed catalyst bed consists of 25 to 75% by volume, relative to the volume of all particles of the fixed bed, of inert particles having a coefficient of heat conductivity at 200° C. of at least 400 $Jh^{-1} cm^{-1} K^{-1}$.

8. The process as claimed in one of claim 1 or 2, wherein the fixed catalyst bed has a free gas space of from 20 to 45% by volume.

9. The process as claimed in one of claims 1 or 2, which comprises introducing the gases into the reaction zone in the following molar ratio: 1 mol $C_2H_4$:0.4 to 0.55 mol $Cl_2$:0.9 to 1.2 mol HCl: 0.25 to 0.4 mol $O_2$.

10. The process as claimed in one of claim 1 or 2, which comprises using from 1.8 to 1.99 mols of Cl per mol of ethylene, calculated on the sum of $Cl_2$ and HCl.

11. The process as claimed in one of claim 1 or 2, which comprises using air, optionally in admixture with oxygen, as oxygen-containing inert gas.

* * * * *